(12) United States Patent
Hatano et al.

(10) Patent No.: US 7,964,392 B2
(45) Date of Patent: Jun. 21, 2011

(54) CULTURE DOUBLE CONTAINER AND A METHOD OF CULTURE

(75) Inventors: Yasushi Hatano, Yokohama (JP); Risaburo Matsuki, Yokohama (JP)

(73) Assignee: Toyo Seikan Kaisha, Ltd., Tokyo (JP)

( * ) Notice: Subject to any disclaimer, the term of this patent is extended or adjusted under 35 U.S.C. 154(b) by 1135 days.

(21) Appl. No.: 11/547,294

(22) PCT Filed: Apr. 7, 2005

(86) PCT No.: PCT/JP2005/007186
§ 371 (c)(1),
(2), (4) Date: Oct. 3, 2006

(87) PCT Pub. No.: WO2005/100536
PCT Pub. Date: Oct. 27, 2005

(65) Prior Publication Data
US 2008/0274536 A1    Nov. 6, 2008

(30) Foreign Application Priority Data

Apr. 13, 2004    (JP) .................... 2004-117776

(51) Int. Cl.
*C12M 1/12* (2006.01)
(52) U.S. Cl. .................................. 435/297.2
(58) Field of Classification Search .......... 435/243, 435/297.1–297.5
See application file for complete search history.

(56) References Cited

U.S. PATENT DOCUMENTS

| 4,734,372 | A | * | 3/1988 | Rotman ........................ 435/29 |
| 5,071,760 | A | * | 12/1991 | Watanabe et al. ............ 435/394 |
| 5,362,642 | A | * | 11/1994 | Kern ............................ 435/404 |
| 5,458,593 | A | * | 10/1995 | Macabasco et al. ......... 604/403 |
| 6,670,174 | B1 | * | 12/2003 | Smith et al. ............... 435/305.4 |

FOREIGN PATENT DOCUMENTS

| JP | 60-27379 | 2/1985 |
| JP | 03-010676 | 1/1991 |
| JP | 03-172169 | 7/1991 |
| JP | 4-71482 A | 3/1992 |

OTHER PUBLICATIONS

PCT Search Report dated Jun. 14, 2005.
PCT Written Opinion dated Jun. 14, 2005.
Japan Patent Office Action Dated Oct. 12, 2010.

* cited by examiner

*Primary Examiner* — Walter D Griffin
*Assistant Examiner* — Shanta G Doe
(74) *Attorney, Agent, or Firm* — Hedman & Costigan, P.C.; James V. Costigan (57) ABSTRACT

A culture container and a method of culture which do not require a plurality of incubators in a case where a plurality of cells of different kinds which like different gas concentrations should be cultured simultaneously.

A culture double container 1 comprises a gas-permeable culture container 2 having an inlet and an outlet 6, a gas-impermeable container 3 covering the culture container 2, and joint portions 12 and 13 for holding the culture container 2 in the gas-impermeable container 3 in such a manner that space is defined between the culture container 2 and the gas-impermeable container 3. The culture double container 1 receives gas controlled in its composition in the space defined houses the culture container 2 and the gas-impermeable container 3 during culture of cell or micro-organism.

12 Claims, 10 Drawing Sheets

CULTURE DOUBLE CONTAINER AND A METHOD OF CULTURE

TECHNICAL FIELD

This invention relates to a culture container for culturing cells or micro-organisms and a method of culture and, more particularly, to a culture container which has excellent capability for preservation of culture medium, achievement of an optimum culture environment and easiness for extracting contents of a culture container and is suitable for culture of floating cell and culture of deposited cell which uses a carrier such as beads or non-woven cloth, and also to a method of culture using this culture container.

BACKGROUND ART

As a culture container for culturing cells, known in the art is a culture bag made of gas-permeable plastic used for filling culture medium therein. For example, Japanese Utility Model Application Laid-open Publication No. Hei 2-93999 discloses a culture bag in which a main body in the form of a bag made of a flexible plastic sheet has, in its upper portion, a solvent injection tube provided with a filter for separating micro-organism and also a culture medium outlet and a sterilized culture medium is filled in the main body of the bag. Japanese Utility Model Application Laid-open Publication No. Hei 3-172169 discloses a preservation and tissue culture container in which air-permeable sealing container for tissue culture containing a culture medium for tissue culture is sealingly wrapped with an impermeable material and this impermeable material is removed during tissue culture. Japanese Patent Application Laid-open Publication No. Hei 4-71482 discloses a method for manufacturing a culture bag filled with culture medium according to which culture medium which has been filtered for sterilization is filled in a sterilizing manner into a culture bag made of a film having large gas permeability and sterilized with γ-ray, the filling inlet is sealed in a sterilizing manner and then the culture bag is wrapped in a sterilizing manner with a secondary wrapping material which has small gas permeability and has been sterilized with γ-ray.

DISCLOSURE OF THE INVENTION

Problem to be Solved by the Invention

Cell culture is usually conducted in an incubator in which gas composition is controlled and, therefore, when it is necessary to culture plural types of cells which like different gas concentrations simultaneously, plural incubators having different gas concentrations become necessary if conventional culture bags are used. This requires a large space and complex and troublesome operations. Moreover, during culture, the conventional culture bags are arranged flatly on a rack in an incubator and cannot be superposed one upon another or suspended perpendicularly and this requires a further large space.

Further, since the conventional culture bags are made of a thin material, they lack stability in the shape and there is likelihood of damage in the course of commercial circulation and therefore handling of the culture bags needs special care which is rather troublesome. In the course of the culture bags disclosed in the above described literature which are wrapped with impermeable wrapping material during preservation, the culture bags are either in floating state inside the wrapping materials and therefore are in an instable shape or in close contact with the outside wrapping material in which case the culture bag as a whole becomes substantially the same as a single layer culture bag. Thus, they are also instable in the shape and there is likelihood of damage in the course of commercial circulation.

Furthermore, when contents are taken out of the culture bags after completion of cell culture, the conventional culture bags are suspended perpendicularly and contents are taken out of the bag by gravity. This requires time and inefficient. If an attempt is made to apply internal pressure to the culture bags to facilitate taking out of the contents, the bags are swollen and this makes it difficult to take out the contents smoothly.

It is therefore an object of the present invention to eliminate the problems of the conventional culture containers and provide a culture container which does not require plural different incubators even when plural types of cells which like different gas concentrations are cultured simultaneously, which can be superposed one upon another or suspended perpendicularly during culture and thereby can save space, which is not likely to be damaged during commercial circulation and therefore is excellent as a container suitable for commercial circulation, and which enables efficient taking out of contents after completion of culture.

It is another object of the invention to provide a method of culture of cells or micro-organisms using the culture container of the present invention.

Means for Solving the Problem

A culture double container achieving the above described objects of the invention comprises a gas-permeable culture container having an inlet and an outlet, a gas-impermeable container covering the culture container, and culture container holding means for holding the culture container in the gas-impermeable container in such a manner that space is defined between the culture container and the gas-impermeable container, said culture double container receiving gas controlled in its composition in the space defined between the culture container and the gas-impermeable container during culture of cell or micro-organism.

In one aspect of the invention, there is provided a culture double container wherein the culture container holding means joins the culture container partially to the gas-impermeable container.

In another aspect of the invention, there is provided a culture double container wherein the gas-impermeable container has a passage for gas which communicates with the space between the culture container and the gas-impermeable container.

In another aspect of the invention, there is provided a culture double container wherein a wall of the culture container is substantially formed during culture in either one of a cylindrical shape, a polygonal case shape having a cross-section of a regular polygon, a spherical shape and a semi-spherical shape.

In another aspect of the invention, there is provided a culture double container wherein culture medium is sealingly filled in the culture container and air in the space between the culture container and the gas-impermeable container is substituted by an inert gas or a mixed gas of an inert gas and carbonic acid gas.

In another aspect of the invention, there is provided a culture double container wherein culture medium is sealingly filled in the culture container and gas in the space between the culture container and the gas-impermeable container is removed.

In another aspect of the invention, there is provided a culture double container wherein culture medium is sealingly filled in the culture container and an oxygen absorbing agent is filled in the space between the culture container and the gas-impermeable container.

In another aspect of the invention, there is provided a culture double container wherein the gas-impermeable container has an oxygen absorbing portion or an oxygen absorbing layer.

In another aspect of the invention, there is provided a method of culture comprising a step of culturing, in a culture double container comprising a gas-permeable culture container having an inlet and an outlet, and a gas-impermeable container covering the culture container, space being defined between the culture container and the gas-impermeable container, by controlling composition of a gas filled in said space.

In another aspect of the invention, there is provided a method wherein the gas which has been controlled in composition is filled in and taken out of a gas passage communicating with the space between the culture container and the gas-impermeable container.

In another aspect of the invention, there is provided a method wherein, in a culturing process, a compressed gas is filled in the space between the culture container and the gas-impermeable container for extracting contents of the culture container.

has air therein substituted by an inert gas or a mixed gas of an inert gas and carbonic acid gas.

ADVANTAGEOUS RESULTS OF THE INVENTION

According to the invention, since gas controlled in its composition is filled in the space defined between the culture container and the gas-impermeable container during cell culture, in a case where plural types of cells which like different gas concentrations are required to be cultured simultaneously, plural culture double containers containing these cells for culture are arranged in a common incubator and gases having necessary gas concentrations are filled in these culture double containers. Thus, cell culture can be performed in a simple manner without requiring plural incubators. Besides, according to the invention, since the space is defined between the culture container and the gas-impermeable container and the culture container is held in the gas-impermeable container by the culture container holding means, in a case where the culture double containers are superposed one upon another during culture, gas can penetrate into each of the culture containers without causing any trouble to culture. Moreover, the culture double container does not change its form when it is suspended perpendicularly, a number of the culture double containers can be suspended in an incubator and therefore can save a lot of space for disposing culture containers as compared with a case where the conventional culture containers are used.

According to the invention, by filling compressed gas such as compressed air in the space between the culture container and the gas-impermeable container after completion of culture, contents of the culture container can be taken out promptly and thus taking out of contents can be performed much more efficiently than the conventional method depending upon gravity.

According to one aspect of the invention, since a wall of the culture container is formed during culture in either one of a cylindrical shape, a polygonal case shape having a cross-section of a regular polygon, a spherical shape and a semi-spherical shape, gas diffuses toward the center of the culture container from 360 degree directions and difference in concentration of gas between a position in the vicinity of the wall of the container and the remotest position from the wall becomes small as compared with the conventional culture container consisting of a flat bag. Consequently, culture condition which is nearer to an optimum culture condition can be achieved whereby efficiency and activity of culture of cells can be improved.

According to still another aspect of the invention, since air in the space between the culture container and the gas-impermeable container is substituted by an inert gas or a mixed gas of an inert gas and carbonic acid gas or air in this space is removed, oxidation of culture medium can be more perfectly prevented whereby preservation time of culture medium can be prolonged. Similarly, by filling an oxygen absorbing agent in this space or providing an oxygen absorbing portion or an oxygen absorbing layer in the gas-impermeable container, similar oxidation prevention effect can be achieved.

BRIEF DESCRIPTION OF THE DRAWINGS

FIGS. 15A and 15B are views showing another embodiment of the present invention in which

DESCRIPTION OF PREFERRED EMBODIMENTS

Preferred embodiments of the invention will now be described with reference to the accompanying drawings.

Figure 1:
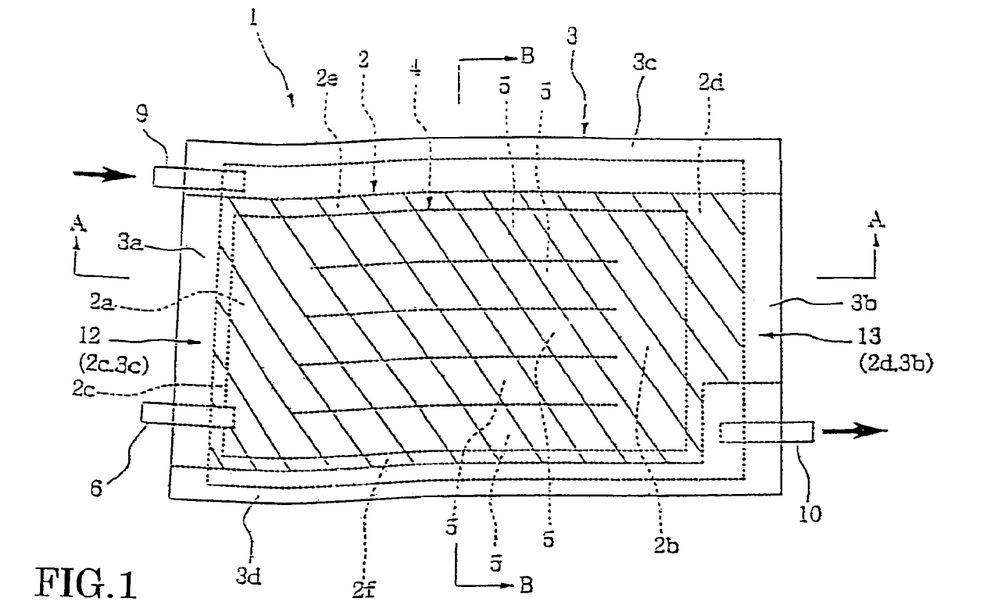
FIG. 1. is a plan view showing an embodiment of a culture double container of the present invention.
Figure 2:
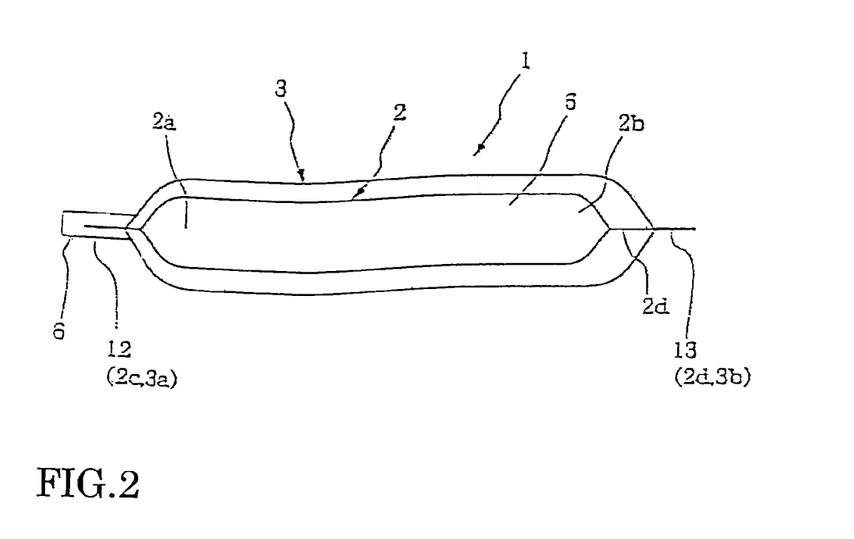
FIG. 2 is a sectional view taken along arrows A-A in FIG. 1.
Figure 3:
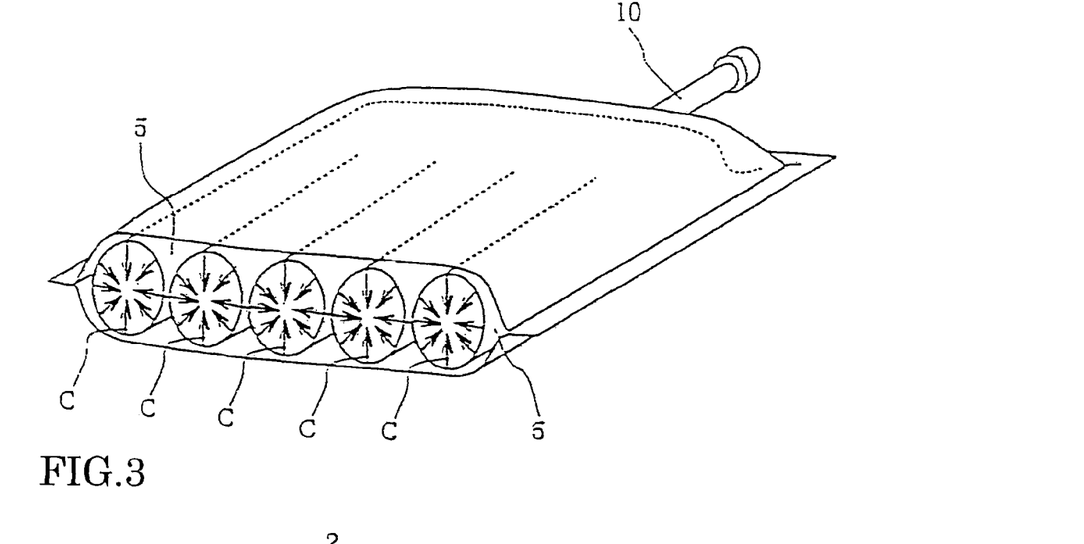
FIG. 3 is a perspective section taken along arrows B-B in FIG. 1.
Figure 4:
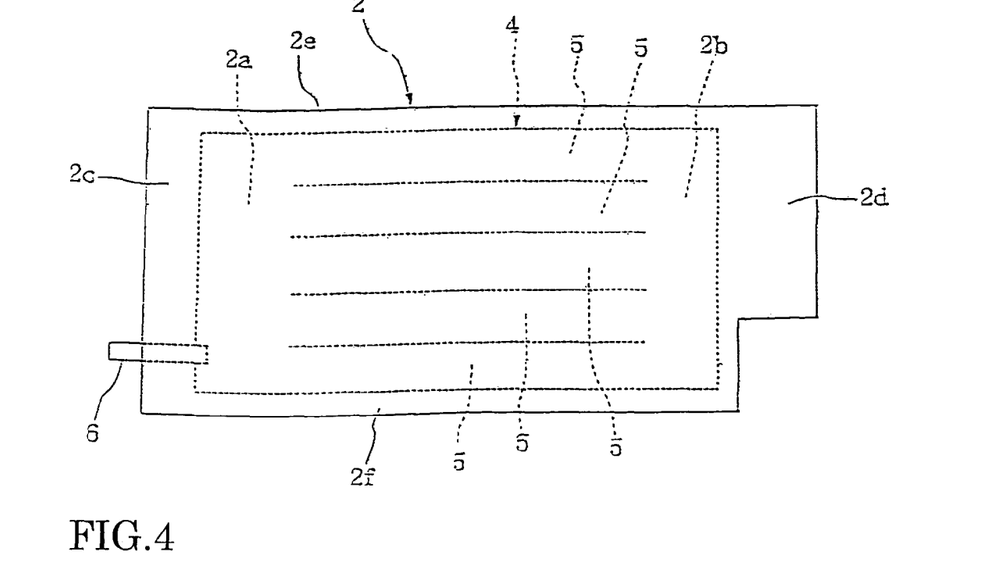
FIG. 4 is a plan view of a culture container.

FIG. 1 to FIG. 4 show an embodiment of the invention wherein FIG. 1 is a plan view, FIG. 2 is a view taken along arrows A-A in FIG. 1, FIG. 3 is a perspective view taken along arrows B-B in FIG. 1 and FIG. 4 is plan view of the culture container.

A culture double container 1 comprises a culture container 2 and a gas-impermeable container 3.

Figure 7A:
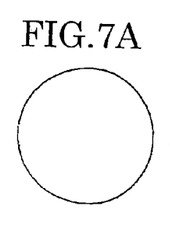
FIGS. 7A to 7E are sections showing shapes of walls of the container.
Figure 7B:
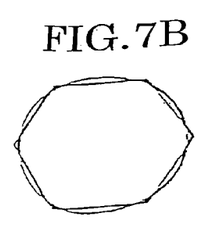
Figure 7C:
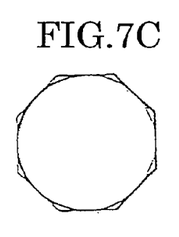
Figure 7D:
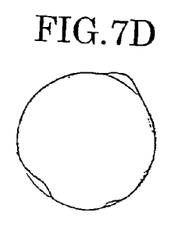
Figure 7E:
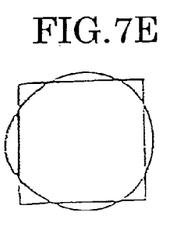

In the present invention, a wall of the culture container 2 should preferably be substantially formed during culture in either one of a cylindrical shape, a polygonal case shape having a cross-section of a regular polygon, a spherical shape and a semi-spherical shape. In the present specification, the shape of "substantially cylindrical" means not only a cylinder having a cross-section of a perfect circle as shown in FIG. 7A but also a cylinder having a cross-section of a circle which is distorted to such a degree as will not obstruct achievement of the object of the invention, e.g., a slightly distorted circle as shown in FIG. 7D or an ellipse. Likewise, the shape of "a polygonal case having a cross-section of a substantially regular polygon" means not only cases having a cross section of a regular polygon such as a regular triangle, a regular square (shown in FIG. 7E), a regular pentagon, a regular hexagon (shown in FIG. 7B) and a regular octagon (shown in FIG. 7C) but also cases having a cross-section of a polygon which is distorted to such a degree as will not obstruct achievement of the object of the invention.

The culture container 2 is a container in the form of a generally rectangular bag as a whole in its plan view which is made of plastic having sufficient gas-permeability and comprises a cylinder section 4 consisting of a plurality (five in the illustrated example) of cylinders 5 arranged in the form of a beach mat and end portions 2a and 2b which are formed adjacent to the end portions in the longitudinal direction of the cylinder section 4. The outer edge portions of the end portions 2a and 2b are respectively closed. The end portions 2a and 2b have flat surfaces and the respective cylinders 5 are communicated with one another via the end portions 2a and 2b. The end portion 2a is provided with an injection-extraction opening 6 for culture medium, cells, cell growth element etc. which communicates with the inside of the culture container 2. The injection-extraction opening 6 may be provided in necessary number for the purpose of culture and a connection tube may be attached to the injection-extraction opening 6 with a connector attached to the tip of a connection tube, if necessary.

Figure 9:
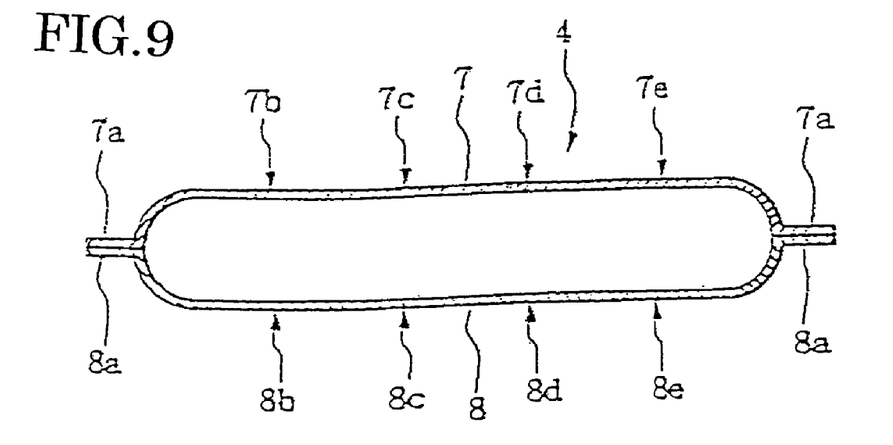
FIG. 9 is a sectional view showing a method for manufacturing a culture container.

For manufacturing the culture container 2, as shown in FIG. 9, rectangular flexible plastic sheets 7 and 8 are disposed face to face with an interval between them and four edge portions 7a and 8a of the sheets 7 and 8 are joined together by heat sealing. Then, the opposing sheets 7 and 8 are partially heat sealed along corresponding longitudinal lines 7b and 8b, 7c and 8c, 7d and 8d and 7e and 8e thereby to form five cylinders 5 which form the cylinder section 4.

By heat sealing the opposing wall surfaces of the soft, flexible culture container 2 and filling culture medium in the container in a predetermined amount, a shape holding property can be imparted to the culture container 2 whereby close contacting between the culture container 2 and the gas-impermeable container 3 can be prevented or reduced and, as a result, obstruction to diffusion of gas to the culture container can be prevented or reduced. As alternative means for imparting the shape holding property to the culture container 2, container holding means such as jigs, clips or magnets may be used to hold the opposing flexible walls of the container so that they will come into partial contact with each other. For preventing or reducing close contact, a member for preventing close contact may be inserted between the walls of the culture container 2 and the gas-impermeable container 3 or projections and depressions may be provided on the respective walls.

As the gas-permeable culture container 2, it is preferable to use a material which has excellent gas permeability and a property to endure sterilization with γ-ray. Such material includes a film bag or a blow bag made of soft plastic such, for example, as polyethylene (PE), polyvinyl chloride (PVC), ethylene vinyl acetate copolymer (EVA), ethylene ethyl acrylate copolymer (EEA), ethylene methyl methacrylate copolymer (EEMA), and a polymer blend of styrene-ethylene-butylene-styrene and polypropylene (PP) or polyethylene.

In a case where γ-ray is not used for sterilization, Teflon (registered trademark), silicone rubber, a single polymer or a copolymer of 4-methyl-1-pentene or a single polymer or a copolymer of butadiene may be used. As other monomer of a copolymer, 2-24 carbon α-olefin or styrene, for example, may be used or a blend of one or more polymers of such α-olefin may also be used.

In the embodiment of FIG. 1, as shown in FIG. 3, gas diffuses in the directions of arrow C, namely toward the center of each cylinder 5 from 360 degree directions and, therefore, difference in concentration of gas between a position in the vicinity of the wall of the container and the remotest position from the wall becomes small and, consequently, culture condition which is nearer to an optimum culture condition can be achieved. During culture, the culture container 2 may be shaken, vibrated or rotated in a level not to give damage to the cell whereby sedimentation of cell or micro-organism observed in culturing of floating cell or micro-organism can be prevented and, moreover, stirring of culture medium is enhanced and this is desirable from the standpoint of maintaining homogeneity.

As will be apparent from FIG. 4, in the portion of the culture container 2 outside of the end portions 2a and 2b in the longitudinal direction of the culture container and in the portions of the culture container outside of the cylinder section 4 in the width direction of the culture container, namely in four edge portions of the culture container 2, there are formed seal portions 2c, 2d, 2e and 2f by heat sealing the two sheets. The seal portion 2d among these seal portions is formed in the shape which is formed by cutting off a portion where a gas extraction opening of the gas-impermeable container 3 is provided as will be explained later so as not to obstruct provision of such gas extraction opening.

The gas-impermeable container 3 is a container having a size which is large enough for forming space which is sufficient for circulating gas between the container 3 and the inside culture container 2. The container 3 is formed generally in a rectangular shape in a plan view with its four edges being closed. The gas-impermeable container 3 may be manufactured by, for example, superposing two gas-impermeable plastic sheets together and heat forming the two sheets so that the central portions is swollen out and seal portions 3a, 3b, 3c and 3d are formed in their four edge portions.

A gas injection opening 9 is provided in one end portion of the gas-impermeable container 3 and a gas exhaustion opening 10 is provided in the other end portion thereof. These openings communicate with the inside of the container 3. Each of the gas injection opening 9 and the gas exhaustion opening 10 constitutes a gas passage of the present invention. The gas passage may be formed as a single opening functioning as both the injection opening 9 and the exhaustion opening 10 concurrently and at least one gas passage and preferably two gas passages are provided. The composition of culture gas may be suitably determined in accordance with the cell or micro-organism to be cultured. The culture gas may be supplied intermittently or continuously. By adjusting pressure of the culture gas, culture in which pressure is applied or culture in which pressure is varied can be realized.

The seal portions 3a and 3b of the gas-impermeable container 3 are fused to the seal portions 2c and 2d of the culture container 2 in such a manner that the seal portions 3a and 3b clamp the seal portions 2c and 2d between them thereby to form joint portions 12 and 13 of the gas-impermeable container 3 and the culture container 2. The joint portions 12 and 13 function to hold the culture container 2 in the gas-impermeable container 3 in such a manner that space is formed between the culture container 2 and the gas-impermeable container 3 and constitute the culture container holding means of the present invention.

Figure 5:
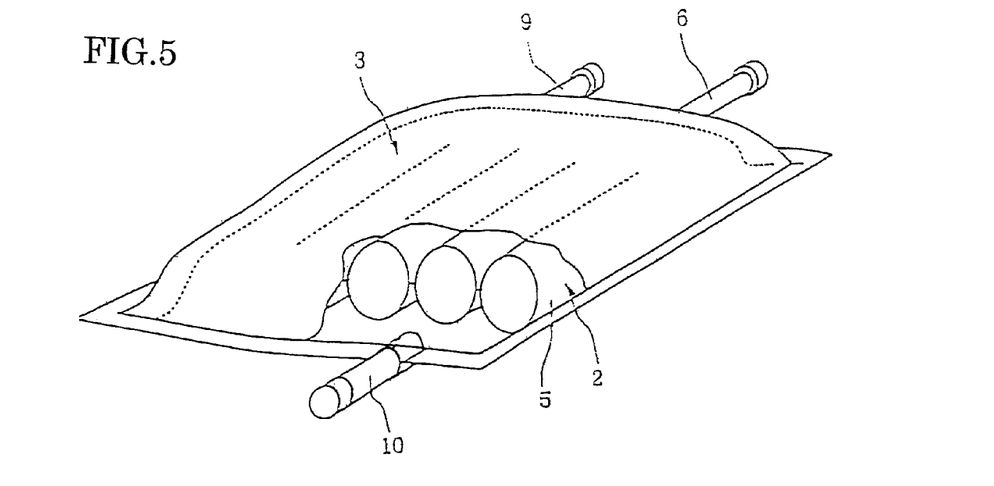
FIG. 5 is a perspective view of a gas-impermeable container shown with a part thereof being cut off for illustrating a gas passage provided during manufacture of the container.
Figure 6:
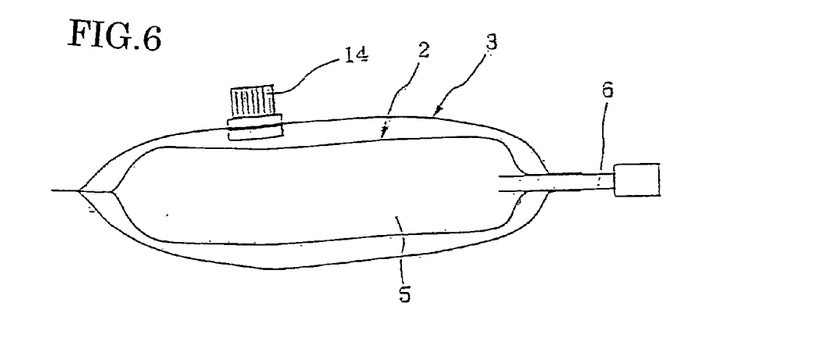
FIG. 6 is a sectional view of a culture double container showing a gas passage attached at a later stage.

The gas passages may be formed previously during manufacture of the culture double container in the end portions the gas-impermeable container 3 as shown in FIG. 5 or, alternatively, a culture double container having no gas passage may be first circulated and, as shown in FIG. 6, a gas passage 14 may be attached to a portion other than the seal portions of the gas-impermeable container 3 at a later stage.

As the gas-impermeable container 3, there is no particular limitation. It may be formed as a blow-bag of a single layer or multiple layers or as a film bag of a single layer or multiple layers. In the case of a blow bag or film bag of a single layer, it should preferably be made of a film of a material which can be heat sealed easily to the surface layer of the culture container and has flexibility, e.g., a plastic film of polyethylene (PE), polypropylene (PP), ethylene-olefin copolymer, ethylene-vinyl acetate copolymer (EVA) etc. It is particularly preferable that the film should be the same material or a material of the same type as the surface layer of the container main body. It is also preferable that the container 3 should be used with an oxygen absorbing agent.

For imparting high impermeability, a multiple layer film is preferable. As a material having gas-impermeability, a multiple layer film of the above described plastic film used as a sealant and one or more of synthetic resin films including, for example, oriented films of a single layer or multiple layers such as a biaxially oriented polyethylene terephthalate film and a biaxially oriented nylon film, a film made of ethylene-vinyl alcohol copolymer (EVOH), polyglycol acid, aromatic polyamide or polyvinylidene chloride (PVDC), polyvinylidene chloride coated films, an alumina-deposited or silica deposited polyester or polyamide film etc.

For laminating these films, a known lamination method such as co-extrusion blow forming, dry lamination, sandwich lamination or extrusion lamination may preferably be used.

In a circulation process of the culture double container 1, preservation property of culture medium can be improved and preservation time thereby can be prolonged by substituting air in the space between the culture container 2 and the gas-impermeable container 3 by an inert gas or a mixed gas of an inert gas and carbonic acid gas, or by removing air in this space. Similarly, a similar effect can be achieved by filling an oxygen absorbing agent in this space or providing an oxygen absorbing portion or an oxygen absorbing layer in the gas-impermeable container 3.

As an oxygen absorbing agent or an oxygen absorbing resin, any known material may be optionally used. As an iron type oxygen absorbing agent, for example, a mixture of iron powder of iron or iron compound and a metal halogenide is preferable. As iron powder, there is no particular limitation in purity or other factors so long as it can produce oxygen absorbing reaction. For example, powder such as reduced iron powder, spray iron powder and electrolytic iron powder, crushed or ground cast iron or steel and powder of iron alloys such as iron carbide, iron carbonyl, ferrous oxide, ferrous hydroxide and iron silicate may be used. Powder of a granular shape is generally preferable and its particle diameter should preferably be within a range from 1 µm to 80 µm and, more preferably, within a range from 1 µm to 50 µm from the standpoints of easiness in handling, thick film thickness of an oxygen absorbing layer and projections and depressions of the oxygen absorbing agent appearing on the film.

As metal halogenide used as an additive to the iron type oxygen absorbing agent, chloride, bromide or iodide of alkali metal or alkaline earth metal may for example be used. Among them, chloride or iodide of lithium, sodium, potassium, magnesium, calcium or barium may preferably be used. A preferable amount of metal halogenide per 100 weight parts of iron powder is 0.1-20 weight parts and, more preferably, 0.1-5 weight parts. It is preferable to add and mix metal halogenide with iron powder previously for preventing separation of the respective materials. A preferable oxygen absorbing agent is an iron powder type composition including iron powder and metal halogenide and, more preferably, a metal halogenide covered iron powder type composition in which metal halogenide is deposited on iron powder.

The iron type oxygen absorbing agent may be filled in the space defined between the gas-permeable culture container 2 and the gas-impermeable container 3 covering it or space communicating with this space in the sate in which the agent is packed in non-woven cloth or paper in a manner not to leak out or may be mixed with a part of resin of a spout or cap constituting the container. Alternatively, it may be used in the form of an oxygen absorbing layer as any desired layer of the gas-impermeable container 3. In this case, the oxygen absorbing layer should preferably be formed in one side or a part only of the gas-impermeable container 3 so that the inside of the gas-impermeable container 3 may be observed.

A preferable amount of the iron type oxygen absorbing agent to the resin is within a range from 10 weight % to 70 weight % and, more preferably, within a range from 10 weight % to 60 weight %. If the amount of the oxygen absorbing agent is less than 10 weight %, sufficient oxygen absorbing capacity cannot be secured whereas if the amount is higher than 70 weight %, processing such as injection molding, compression molding and film forming may become difficult. A preferable thickness of film of the oxygen absorbing layer is within a range from 10 µm to 100 µm and, more preferably, within a range from 20 µm to 80 µm regardless of the material of the film. If the thickness of the film is less than 10 µm, an oxygen absorbing amount per unit area of the film becomes small and sufficient oxygen absorbing capacity may not be secured. If the thickness of the film exceeds 100 µm, total thickness of the film becomes large with resulting inconvenience in handling and occurrence of a cost problem.

As the oxygen absorbing resin, a resin comprising a metal type oxidative catalyst and oxidative resin or oxidative organic ingredient, or a resin comprising polyphenols, ascorbic acids or the like and a basic material may be used.

As the oxidative resin or oxidative organic ingredient, a resin or organic ingredient which is subject to oxidation by oxygen in the air under the action of a transition metal type catalyst may be used.

As the oxidative resin may be used (1) a resin having class 3 carbon such as polypropylene, (2) a resin having a carbonyl group such as ethylene-carbon monoxide copolymer, (3) a polyamide resin having benzene ring such as MXD 6, (4) a resin having an unsaturated double bond in a main chain such as polybutadiene, polyisoprene and their copolymers, (5) a resin having an unsaturated double bond in a side chain such as cyclohexane group, and (6) a cyclic conjugated diene type resin such as polycyclohexadiene. As the oxidative organic ingredient may be cited (7) ascorbic acid and (8) cystein. They absorb water and oxygen under coexistence with a basic material such as sodium carbonate and potassium acetate.

As the metal type oxidative catalyst, metal compounds of Group VIII such as iron, cobalt and nickel are preferable. Other metal compounds such as copper and silver (Group I), tin, titanium and zirconium (Group IV), vanadium (Group V), chromium (Group VI) and manganese (Group VII) may also be used. Among these metal compounds, cobalt compound is particularly preferable because of its high oxygen absorbing speed. The transition metal catalyst is generally used in the form of an inorganic salt or organic salt of low valence or complex salt of the above described transition metals. These catalysts may preferably used in an amount of 100 ppm to 2000 ppm for each resin.

The oxidative resin or oxidative organic ingredient is advantageous over the iron type oxygen absorbing agent in that it can be applied without impairing observing capability and may be used as an oxygen absorbing layer in a desired portion or in entire surface of either one or both of the gas-permeable culture container 2 and the gas-impermeable container 3. It may also be mixed with a part of resin of a desired container constituting component such as a spout or cap which is positioned in the space between the culture container 2 and the gas-impermeable container 3 or space communicating with this space.

In the case of providing the oxygen absorbing layer in the gas-impermeable container 3, the container 3 may be formed in any desired structure, such, for example and not limited thereto, as an oxygen absorbing layer (single layer only), an outer layer and an oxygen absorbing layer (two layers), an outer layer, an oxygen absorbing layer and a sealant layer, an outer layer, a gas-impermeable layer and a sealant layer, and an outer layer, a gas-impermeable layer, an oxygen absorbing layer, a gas impermeable layer and a sealant layer.

For manufacturing the culture double container of the present embodiment, a culture double container filled with an oxygen absorbing agent if necessary is produced and then is subjected to sterilization by γ-ray (or sterilization by ultraviolet ray, electron ray or heating etc.). Then, culture medium is filled in the container and the filling opening of the container is sealed in a sterilizing manner to complete the manufacture.

Figure 8A:
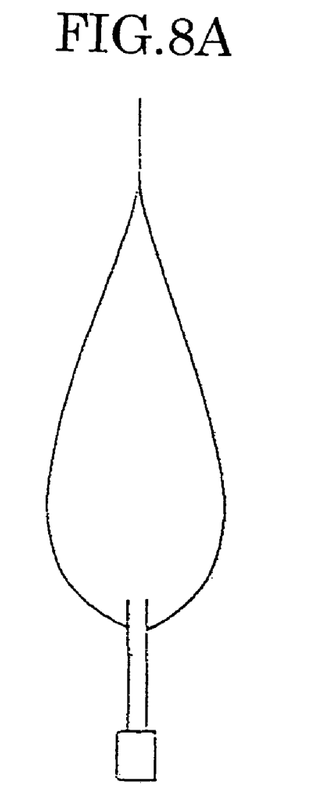
FIGS. 8A and 8B are side sectional views of a prior art container and the culture double container of the present invention shown respectively in a perpendicularly suspended state.
Figure 8B:
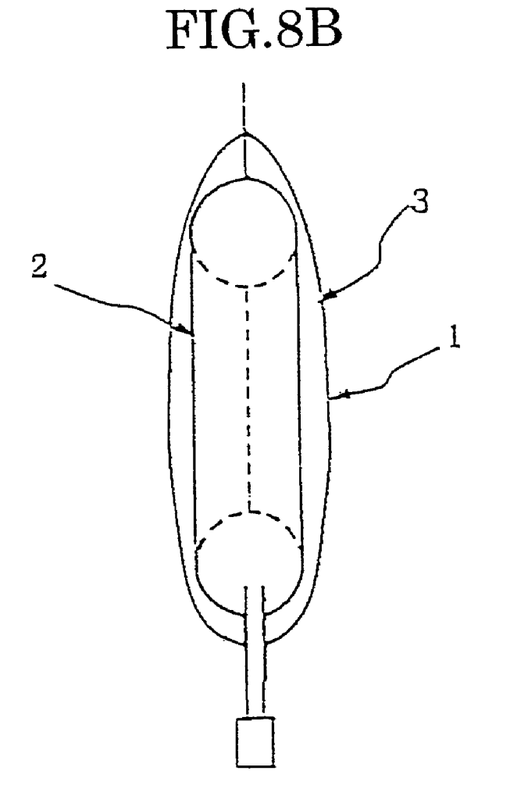

In the case of the conventional container, if it is suspended perpendicularly, its shape is changed as shown in FIG. 8A and lack of uniformity in diffusion of gas becomes serious between a position in the vicinity of the wall of the container and the remotest position from the wall and an optimum gas composition therefore cannot be realized. For this reason, it cannot be suspended in this manner. In the case of the culture double container of the present embodiment, if the culture double container is suspended perpendicularly as shown in FIG. 8B during culture, the shape of the container remains unchanged. Accordingly, a number of the culture double containers 1 can be arranged in the perpendicularly suspended state whereby space for disposing the culture double containers can be saved.

Figure 10:
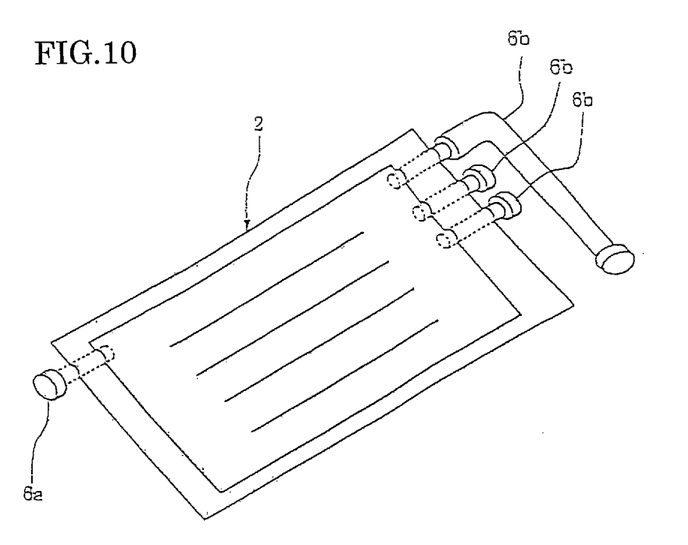
FIG. 10 is plan view of a culture container of another embodiment of the culture double container of the present invention.
Figure 11:
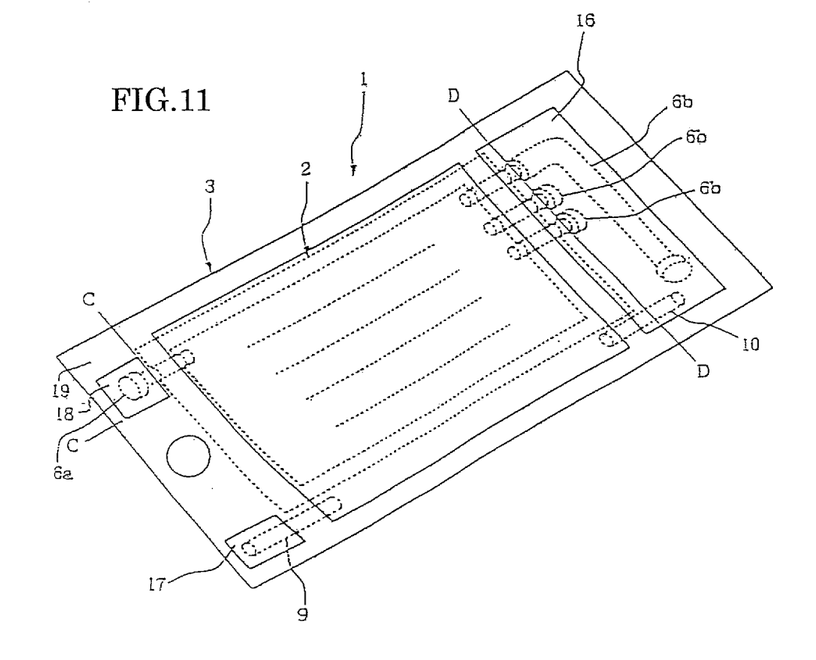
FIG. 11 is a plan view of the other embodiment of the culture double container of the present invention.

FIGS. 10 and 11 show another embodiment of the culture double container of the present invention. In this embodiment, a culture container 2 provided with an injection-extraction openings 6a and 6b is produced and then two sheets of gas-impermeable materials are heat sealed to the culture container 2 in a manner to cover the culture container 2 as shown in FIG. 11 to form a gas-impermeable container 3 and thereby manufacture a culture double container 1.

In this embodiment, an injection-extraction openings and gas exhaustion opening housing section 16, a gas injection opening housing section 17 and an injection-extraction opening housing section 18 are first provided. A portion 19 including the injection and extraction opening housing section 18 and being defined by lines C-C is formed as an unsealed portion while injection-extraction openings 6a and 6b, a gas injection opening 9 and a gas exhaustion opening 10 are covered with an impermeable material constituting the gas-impermeable container 3. In this case, an oxygen absorbing agent may be filled in the injection and extraction openings and gas exhaustion opening housing section 16. By this arrangement, a function of removing oxygen in the container main body can be imparted via the gas exhaustion opening 10 and the oxygen absorbing agent may be removed during use of the container.

Then, one or more of the culture double containers produced in this manner are put in a sterilizing bag and is subjected to sterilization. Then, the bag is opened in a sterilized environment and culture medium is filled in a sterilizing manner through the injection-extraction opening 6a provided in the unsealed portion 19 and is opened along lines C-C and this portion is sealed in a sterilizing manner. The container is then heat sealed leaving the injection-extraction opening housing section 18 to make a culture double container. By this arrangement, the injection-extraction openings 6a and 6b are advantageously protected by the impermeable material.

During use of the container, the extraction opening and gas exhaustion opening housing section 16 is opened along line D-D. Since the injection-extraction openings 6b are already maintained in a sterilized state by the sterilization by γ ray, there is the advantage that the outside portion only has to be sterilized and the injection-extraction openings 6b need not be sterilized.

In a case where the gas exhaustion opening 10 is used also as the gas injection opening 9, the gas injection opening 9 and the gas injection opening housing section 17 need not be provided and even if they are provided, the housing section 17 need not be opened.

Figure 12:
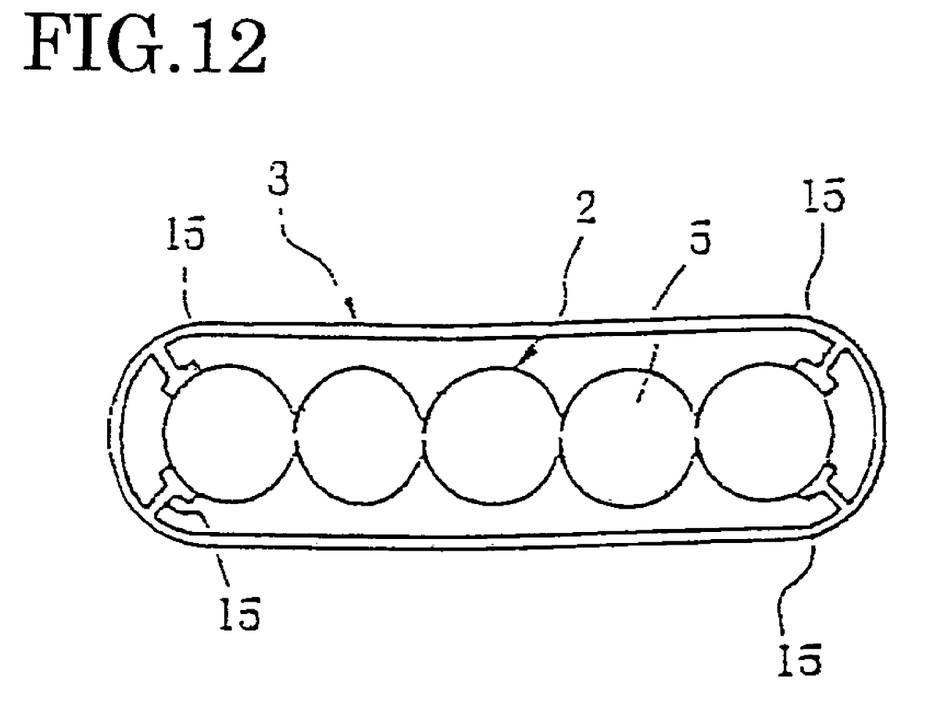
FIG. 12 is a sectional view showing another example of the culture container holding means.

In the previously described embodiment, the culture container holding means is constituted by the joint portions 12 and 13 but the culture container holding means is not limited to such joint means but, as shown in the sectional view of FIG. 12, culture container support arms 15 which support the culture container 2 by abutting against outside four corners of the culture container 2 may be formed in the longitudinal direction of inside four corners of the gas-impermeable container 3 made of rigid plastic. Any means may be employed as the culture container holding means if it can hold the culture container 2 in the gas-impermeable container 3 in such a manner that space is defined between the culture container 2 and the gas-impermeable container 3.

In the above described embodiments, the culture containers are arranged in parallel in the form of a beach mat. Alternatively, the culture container may consist of a single cylinder. Likewise, in case the container wall is formed in the shape of a polygonal case, a sphere or a hemisphere, various modifications may be conceived.

Each of the culture container and the gas-impermeable container may be formed in the form of a pouch made of soft flexible plastic, or a container having rigidity such as a bottle or may be a combinations of these.

FIGS. 13 to 17 are sectional views of other embodiments of the present invention shown in the same section as FIG. 2. In the embodiment of FIG. 3, the culture containers 2 are heat sealed with adjacent culture containers in their opposite walls in the form of a beach mat thereby to impart the shape holding property. In FIGS. 13 to 17, heat sealing is not made in the culture container 2 and the shape holding property is not imparted to the culture container 2. In the present invention, any means may be adopted if space is defined between the culture container 2 and the gas-impermeable container 3 to prevent or reduce obstruction to diffusion of gas to the culture container 2 and the culture container 2 can be held in the gas-impermeable container 3. Explanation will be made about FIGS. 13 to 17 which show examples of such means. In FIGS. 13 to 17, the same component parts as those shown in the embodiments of FIGS. 1 to 12 are shown by the same reference characters and description thereof will be omitted.

Figure 13:
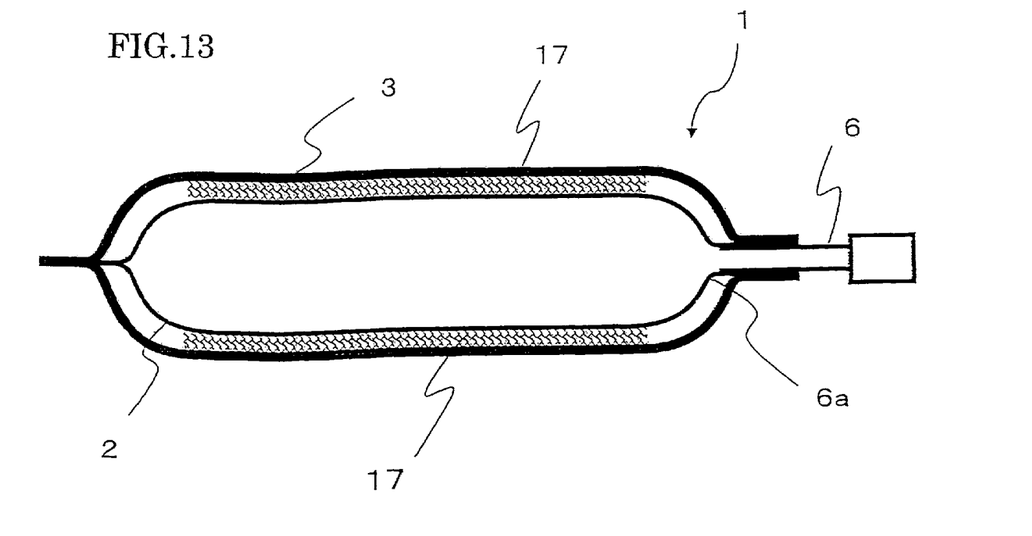
FIG. 13 is a sectional view showing another embodiment of the present invention.

In the embodiment of FIG. 13, the gas-impermeable container 3 is a container made of plastic having rigidity and the gas-permeable culture container 2 is a container made of soft flexible plastic. A gas-permeable mat 17 made of a material having gas permeability such as non-woven cloth is filled between the containers 2 and 3. By this gas-permeable mat 17, space for housing gas controlled in its composition is defined between the containers 2 and 3. In the cell culture process, it is necessary to observe growth capacity of cells with a microscope or the like and, therefore, the gas-permeable mat 17 need not necessarily be provided over the entire surfaces of the containers but a part thereof may be omitted. In short, it may be provided within a range capable of performing its function. For preventing shifting of the gas-permeable mat 17, it may be adhered or fixed to the gas-impermeable container 3 by any known means. In this embodiment, the inner end portion 6a of a culture medium injection-extraction opening 6 is not projecting into the inside portion of the culture container 2 and this is advantageous in that, when culture medium is taken out, there is no possibility that a part of the culture medium is left in the culture container 2.

Figure 14:
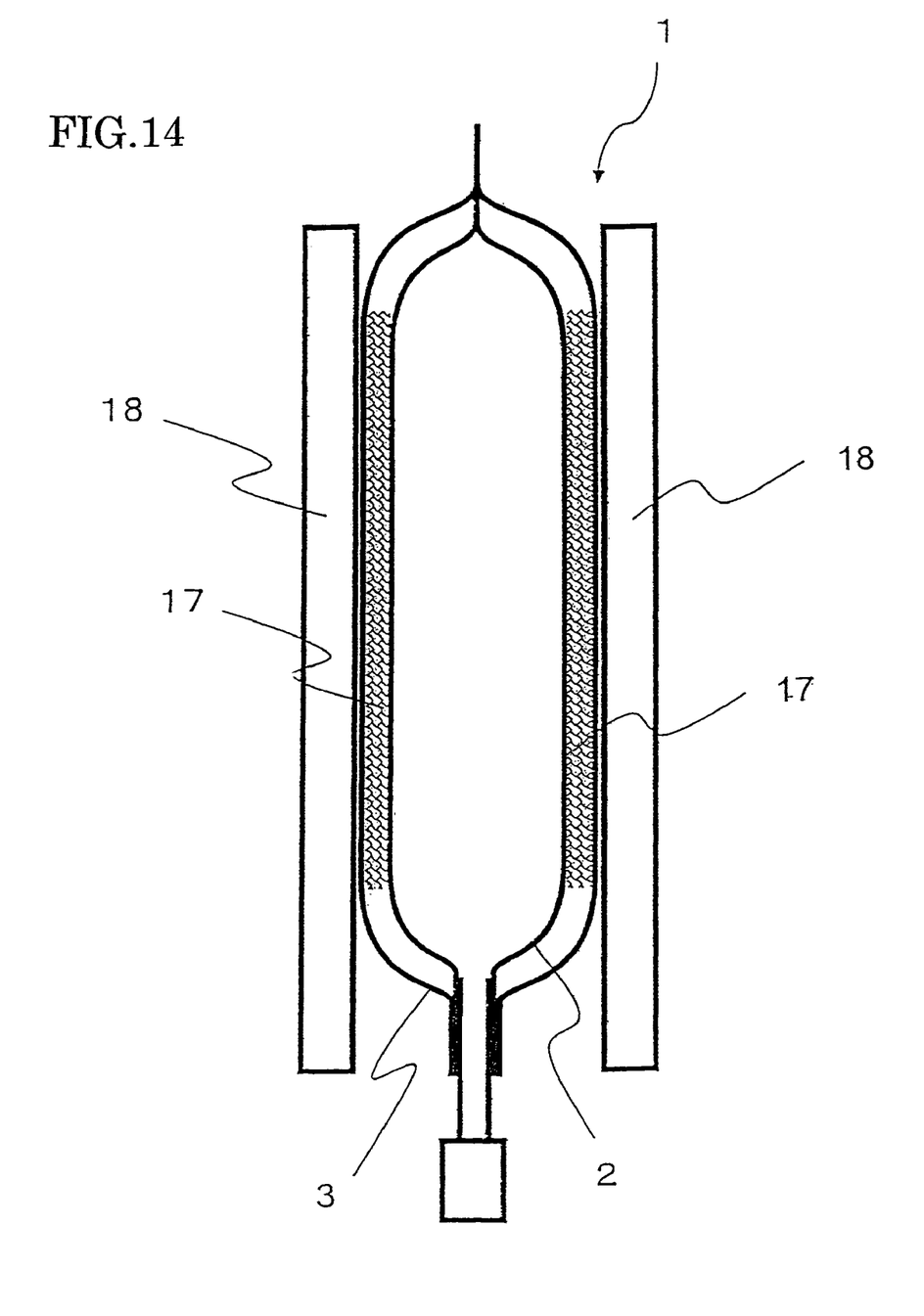
FIG. 14 is a sectional view showing another embodiment of the present invention.

In the embodiment of FIG. 14, both the gas-impermeable container 3 and the culture container 2 are made of soft flexible plastic and the gas-permeable mat 17 is filled between the containers 2 and 3 to defined space for housing gas. In the case of suspending this double container 1 perpendicularly, the container is supported on both sides thereof by reinforcing jigs 18 made of rigid members such as plates or a plurality of bars. By this arrangement, the same effect as shown in FIG. 8B can be obtained whereby the shape holding property can be imparted without requiring the culture container 2 made in the form of a beach mat.

Figure 15A:
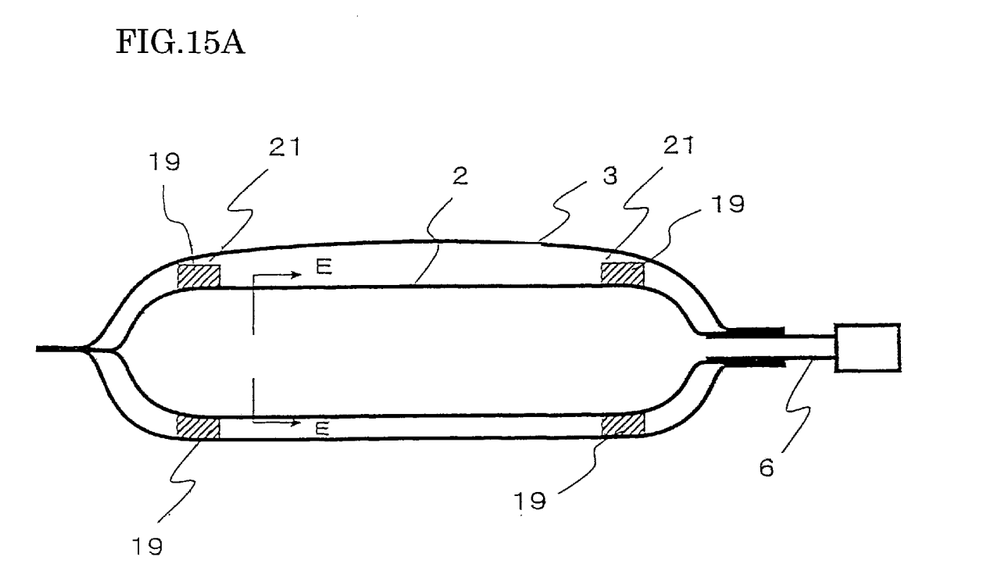
FIG. 15A is a sectional view and FIG. 15B is a perspective section taken along arrows E-E in FIG. 15A.
Figure 15B:
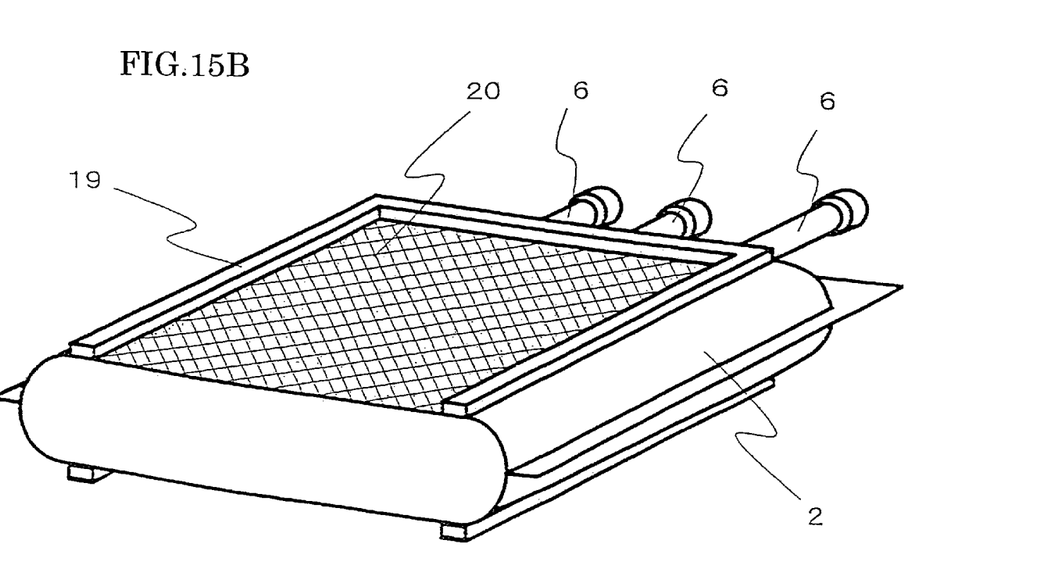

In the embodiment shown in the sectional view of FIG. 15A and FIG. 15B which is a perspective sectional view taken along arrows E-E of FIG. 15A, both the gas-impermeable container 3 and the culture container 2 are made of soft flexible plastic. Reinforcing jigs 19 each of which consists of a rectangular rigid frame member and a net 20 stretched over the frame member are interposed between peripheral edge portions of the inner flat surfaces of the container 3 and peripheral edge portions of the outer flat surfaces of the container 2 and space for housing gas is defined between the containers 2 and 3 by these reinforcing jigs 19. The inner surfaces of the gas-impermeable container 3 are not fixed to the reinforcing jigs 19 so that a gap 21 can be formed between the inner surfaces of the container 3 and the outside surfaces of the reinforcing jigs 19. By this arrangement, in a case where contents of the culture container is taken out by filling compressed gas in the space between the containers 2 and 3, the compressed gas can be circulated without obstruction.

Figure 16:
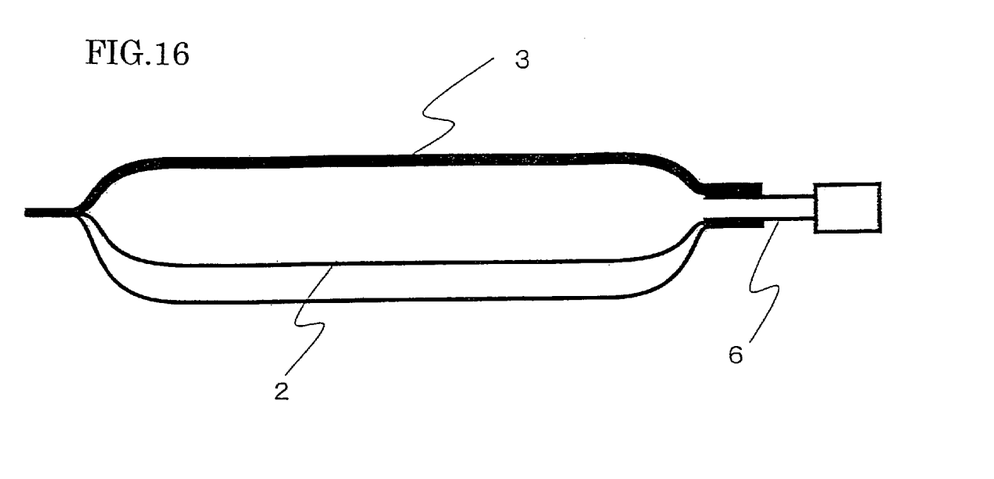
FIG. 16 is a sectional view showing another embodiment of the present invention.
Figure 17:
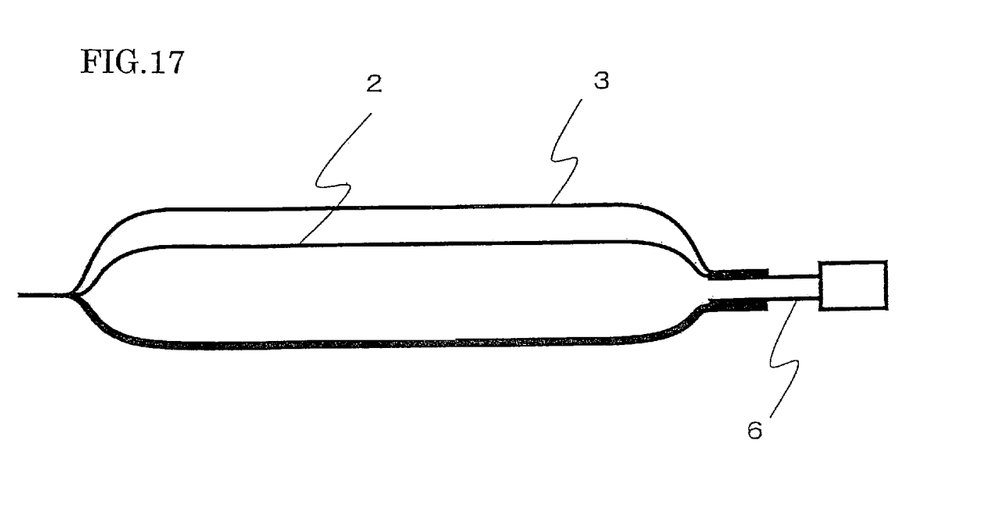
FIG. 17 is a sectional view showing still another embodiment of the present invention.

In each of the embodiments of FIGS. 16 and 17, the gas-impermeable container 3 is made of rigid plastic in one side only and the other side is made of soft flexible plastic. The gas-permeable culture container 2 is made of soft flexible plastic. The side of the culture container 2 facing the rigid side of the gas-impermeable container 3 is adhered closely to the inside of the gas-impermeable container 3 and space for housing gas is defined only between the other side of the culture container 2 and the inside of the soft side of the gas-impermeable container 3. In these embodiments, walls of both sides of the gas-impermeable container 3 may be made soft and flexible or rigid according to necessity.

INDUSTRIAL UTILITY

The present invention is applicable to a culture container for cells or micro-organisms and a method of culture. Particularly the present invention is applicable to a culture container which has excellent capability for preservation of culture medium, achievement of an optimum culture environment and easiness for extracting contents of a culture container and is suitable for culture of floating cell and culture of deposited cell which uses a carrier such as beads or non-woven cloth, and also to a method of culture using this culture container.

What is claimed is:

1. A culture double container comprising a gas-permeable culture container having an inlet and an outlet for cells or micro-organisms and for culture medium and passing gas, a gas-impermeable container covering the culture container, and culture container holding means for holding the culture container in the gas-impermeable container in such a manner that space is defined between the culture container and the gas-impermeable container, said culture double container receiving cells or micro-organisms, and culture medium in the gas permeable culture container and receiving gas controlled in its composition in the space defined between the culture container and the gas-impermeable container during culture of cell or micro-organism wherein said culture container is a container in the form of a generally rectangular bag in its plan view which is made of plastic and comprises a cylinder section consisting of a plurality of cylinders arranged in the form of a beach mat with end portions being formed adjacent to end portions in the longitudinal direction of the cylinder section, said end portions of the culture container having flat surfaces, outer edge portions of said end portions being respectively closed, and the respective cylinders being communicated with one another via the end portions.

2. A culture double container as defined in claim 1 wherein the culture container holding means joins the culture container partially to the gas-impermeable container.

3. A culture double container as defined in claim 1 wherein the gas-impermeable container has a passage for gas which communicates with the space between the culture container and the gas-impermeable container.

4. A culture double container as defined in claim 1 wherein, a wall of the culture container is substantially formed during culture in either one of a cylindrical shape, a polygonal case shape having a cross-section of a regular polygon, a spherical shape and a semi-spherical shape.

5. A culture double container as defined in claim 1 wherein culture fluid is sealingly filled in the culture container and air in the space between the culture container and the gas-impermeable container is substituted by an inert gas or a mixed gas of an inert gas and carbonic acid gas.

6. A culture double container as defined in claim 3 wherein culture fluid is sealingly filled in the culture container and air in the space between the culture container and the gas-impermeable container is substituted by an inert gas or a mixed gas of an inert gas and carbonic acid gas.

7. A culture double container as defined in claim 1 wherein culture fluid is sealingly filled in the culture container and air in the space between the culture container and the air impermeable container is removed.

8. A culture double container as defined in claim 1 wherein culture fluid is sealingly filled in the culture container and an oxygen absorbing agent is filled in the space between the culture container and the air impermeable container.

9. A culture double container as defined in claim 1 wherein the gas-impermeable container has an oxygen absorbing portion or an oxygen absorbing layer.

10. A method of culture comprising, in a culture double container comprising a gas-permeable culture container having an inlet and an outlet for cells or micro-organisms and for culture medium and passing gas, and a gas-impermeable container covering the culture container, space being defined between the culture container and the gas-impermeable container said culture double container receiving cells or micro-organisms, and culture medium in the gas-permeable container and receiving gas in the space during culture of cells or micro-organisms, a step of culturing, by controlling composition of the gas filled in said space wherein said culture container is a container in the form of a generally rectangular bag in its plan view which is made of plastic and comprises a cylinder section consisting of a plurality of cylinders arranged in the form of a beach mat with end portions being formed adjacent to end portions in the longitudinal direction of the cylinder section, said end portions of the culture container having flat surfaces, outer edge portions of said end portions being respectively closed, and the respective cylinders being communicated with one another via the end portions.

11. A method as defined in claim 10 wherein the gas which has been controlled in composition is filled in and taken out of a gas passage communicating with the space between the culture container and the gas-impermeable container.

12. A method as defined in claim 10 or 11 wherein, in a culturing process, a compressed gas is filled in the space between the culture container and the gas-impermeable container for extracting contents of the culture container.

* * * * *